United States Patent
Beech et al.

(10) Patent No.: US 9,138,482 B2
(45) Date of Patent: Sep. 22, 2015

(54) PHARMACEUTICAL FORMULATION COMPRISING NSAID AND CYCLODEXTRIN

(75) Inventors: Edward Beech, Hull (GB); Alden Rodwell, Hull (GB); Mark Squires, Hull (GB)

(73) Assignee: Reckitt Benckiser Healthcare International Limited, Slough, Berkshire (GB)

(*) Notice: Subject to any disclaimer, the term of this patent is extended or adjusted under 35 U.S.C. 154(b) by 6 days.

(21) Appl. No.: 13/993,320

(22) PCT Filed: Dec. 12, 2011

(86) PCT No.: PCT/GB2011/052457
§ 371 (c)(1),
(2), (4) Date: Jul. 2, 2013

(87) PCT Pub. No.: WO2012/080718
PCT Pub. Date: Jun. 21, 2012

(65) Prior Publication Data
US 2014/0296342 A1 Oct. 2, 2014

(30) Foreign Application Priority Data
Dec. 15, 2010 (GB) .................................. 1021267.8

(51) Int. Cl.
| A61K 31/192 | (2006.01) |
| A61K 47/40 | (2006.01) |
| A61K 31/196 | (2006.01) |
| A61K 47/02 | (2006.01) |
| A61K 9/00 | (2006.01) |
| A61K 9/08 | (2006.01) |
| A61K 9/12 | (2006.01) |
| A61K 47/48 | (2006.01) |
| B82Y 5/00 | (2011.01) |

(52) U.S. Cl.
CPC ................. *A61K 47/40* (2013.01); *A61K 9/006* (2013.01); *A61K 9/08* (2013.01); *A61K 9/12* (2013.01); *A61K 31/192* (2013.01); *A61K 31/196* (2013.01); *A61K 47/02* (2013.01); *A61K 47/48969* (2013.01); *B82Y 5/00* (2013.01)

(58) Field of Classification Search
CPC ........ A61K 47/40; A61K 31/192; A61K 9/006
See application file for complete search history.

(56) References Cited

U.S. PATENT DOCUMENTS

| 5,024,997 | A | 6/1991 | Motola et al. |
| 2007/0232567 | A1 | 10/2007 | Wright |

FOREIGN PATENT DOCUMENTS

| CN | 101559077 A | 10/2009 |
| EP | 0490193 A1 | 6/1992 |
| EP | 1574221 A | 9/2005 |
| EP | 1574221 A1 | 9/2005 |
| EP | 1974751 A1 | 10/2008 |
| JP | 56034618 A | 8/1979 |
| WO | 9200725 A1 | 1/1992 |
| WO | 9200725 A2 | 1/1992 |
| WO | 9504528 A2 | 2/1995 |
| WO | 9507104 A1 | 3/1995 |
| WO | 9718245 A1 | 5/1997 |
| WO | 9718802 A1 | 5/1997 |
| WO | 9852540 A1 | 11/1998 |
| WO | 2004050123 A2 | 6/2004 |
| WO | 2005079858 A1 | 9/2005 |
| WO | 2009089269 A1 | 7/2009 |

OTHER PUBLICATIONS

Moore, N., Dr. et al, "Tolerability of Ibuprofen, Aspirin and Paracetamol for the Treatment of Cold and Flu Symptoms and Sore Throat Pain," IJCP, vol. 56, No. 10, Dec. 2002, pp. 732-734, Publication No. XP009031180.
Guan, P. et al., WPI/Thomson, vol. 2009, Nr: 73, Publication No. XP-002674166.
Kiyoshi Masuda, "Protective Effects of Cyclodextrin for the Local Irritation Induced by Aqueous Preparations of Flurbiorofen," Yakugaku Zasshi, Feb. 1, 1984, pp. 1075-1082.
International Search Report and Written Opinion mailed May 3, 2012 for priority application PCT/GB2011/052457.
CSER issued Mar. 11, 2011 for priority GB application 1021267.8.
CSER issued Mar. 20, 2012 for priority GB application 1121476.4.
Ozaki et al, Transdermal ketoprofen mitigates the severity of postoperative sore throat, Canadian Journal of Anesthesia, vol. 48, No. 11, Dec. 1, 2001, pp. 1080-1083.

*Primary Examiner* — James D Anderson
(74) *Attorney, Agent, or Firm* — Troutman Sanders LLP; Ryan A. Schneider; Troy S. Kleckley

(57) ABSTRACT

The present invention provides a liquid composition in comprising an aqueous solution of an NSAID and one or more cyclodextrins.

36 Claims, 3 Drawing Sheets

PHARMACEUTICAL FORMULATION COMPRISING NSAID AND CYCLODEXTRIN

CROSS-REFERENCE TO RELATED APPLICATIONS

This application is a US National Stage of International Application No. PCT/GB2011/052457, filed 12 Dec. 2011, which claims the benefit of GB 1021267.8, filed 15 Dec. 2010, both herein fully incorporated by reference.

The present invention is directed to a pharmaceutical composition in the form of a spray/aerosol which can be used to deliver unpalatable compounds, such as NSAIDs. In particular, the present invention is directed to a flurbiprofen-based spray.

Flurbiprofen is a member of the phenylalkanoic acid derivative family of non-steroidal anti-inflammatory drugs (NSAIDs) used to treat inflammation and pain. It is predominately used in the treatment of rheumatoid arthritis due to its anti-inflammatory effect.

Flurbiprofen is very insoluble in low pH aqueous solution, and its solubility increases slightly as the pH increases. Flurbiprofen has varying solubility in different organic solvents. Different formats and applications of flurbiprofen have been developed, such as flurbiprofen lozenges used in the treatment of sore throats. Mouthwashes containing flurbiprofen have also been developed; as well as mouth sprays that deliver a low (<0.5% w/v) level of the active Flurbiprofen is known for producing a burning sensation in the buccal cavity (the mouth). This flurbiprofen related burn is extremely unpleasant causing an irritating prickly sensation at the back of the throat as well as a cough, gag, tickle or irritation depending on its concentration. It is desirable to reduce this 'burn' in flurbiprofen-containing products, and there has been considerable effort in this area. For example, there has been much effort in developing flavours that mask the burn with various flavours. The absence of taste receptors at the back of the throat and the ineffectiveness of flavours to cover the burn appear to confirm that the issue to be addressed is the irritating effect of flurbiprofen on pain receptors at the back of the throat.

Cyclodextrins are a family of compounds which are saccharide polymers. These sugar derivatives are formed from differing numbers of sugars bound together to form a cyclic oligosaccharide. As can be seen below α-CD consists of 6 membered sugar ring while β-CD and γ-CD consist of a 7 and 8 membered sugar ring respectively. Cyclodextrins are produced from starch by means of enzymatic conversion. The cyclic structure provides the cyclodextrin molecule with a large surface area, and also allows other smaller molecules to enter it forming an inclusion complex; this provides endless potential uses for cyclodextrins The cyclodextrin's ability to form complexes by "encapsulating" other molecules has plenty of applications, such as in drug delivery systems.

The present invention provides a significantly higher concentration of NSAID per fluid volume than compositions that are currently available.

According to a first aspect of the present invention there is provided a liquid composition in comprising an aqueous solution of an NSAID and one or more cyclodextrins.

Typically the NSAID is selected from the group consisting of ibuprofen, ketoprofen, flurbiprofen, diclofenac, naproxen. Preferably the NSAID can be selected from ketoprofen or flurbiprofen. Most preferably the NSAID is flurbiprofen.

The cyclodextrin can be selected from α, β, γ cyclodextrin and derivatives thereof. Cyclodextrins for use in the present invention include the natural cyclodextrins and their derivatives, including the alkylated and hydroxyalkylated derivatives and the branched cyclodextrins. derivatives bearing sugar residues are of special interest. Especially useful herein are the hydroxyethyl, hydroxypropyl (including 2- and 3-hydroxypropyl) and dihydroxypropyl ethers, their corresponding mixed ethers and further mixed ethers with methyl or ethyl groups, such as methyl-hydroxyethyl, ethyl-hydroxyethyl and ethyl-hydroxypropyl ethers of α, β, γ,-cyclodextrin. Specific cyclodextrin derivatives for use herein include methyl α cyclodextrin, hydroxyethyl α cyclodextrin, hydroxypropyl α cyclodextrin, dihydroxypropyl α cyclodextrin, methyl β cyclodextrin, hydroxyethyl β cyclodextrin, hydroxypropyl β cyclodextrin, dihydroxypropyl β cyclodextrin, methyl γ cyclodextrin, hydroxyethyl γ cyclodextrin, hydroxypropyl γ cyclodextrin and dihydroxypropyl γ cyclodextrin.

The ratio of the NSAID to cyclodextrin is between 1:0.5 and 1:1.5. The ratio can be between 1:0.7 and 1:1. A preferred ratio is 1:0.87. For the avoidance of doubt, the ratios for NSAID and cyclodextrin are molar ratios.

The composition comprises the NSAID at a level of at least 1% w/v. The composition can contain 1-5% w/v. The composition preferably contains no more than 3.2% NSAID. The composition can contain A most preferred amount of NSAID is 1.6% w/v. In an alternative embodiment the preferred amount is 3.13% NSAID.

Typically the composition contains a buffer. The term "buffer" refers to a pharmaceutically acceptable excipient that helps to maintain the pH of the solution within a particular range specific to the buffering system. The buffer is present for example at a concentration in the range from about 0.03% to about 5.0% w/v, or about 0.1% to about 2.0% w/v. Non-limiting illustrative examples of pharmaceutically acceptable buffering agents include phosphates, ascorbates, acetates, citrates, tartrates, lactates, succinates, amino acids and maleates. Particularly preferred buffers are disodium hydrogen orthophosphate, citric acid or combinations thereof.

The pH of a composition in preferred embodiments is generally from about 6 to about 9. Typically, the pH of the liquid formulation is about 7.4. Alternatively, the pH of the liquid formulation may be selected from the following ranges: 6.5 to 8.5; 7.0 to 8.0; and 7.2 to 7.6.

The composition can further contain a thickening agent such as hydroxy ethyl cellulose, hydroxy propyl methyl cellulose, sodium carboxy methyl cellulose or hydroxy propyl cellulose.

Minor amounts of other ingredients such as pH adjusters (e.g., a base such as NaOH), emulsifiers or dispersing agents, preservatives, sweeteners, and flavourants may also be present.

A preferred composition according to the present invention comprises:
(a) 1-5% flurbiprofen;
(b) 5-10% one or more α, β, γ cyclodextrins and derivatives thereof;
(c) up to 5% one or more aqueous buffers;
(d) 80-90% Water.

The composition may further comprise up to 1% one or more flavourants, up to 0.2% sweetener and up to 0.5% preservatives.

The composition may further comprise up to 0.5% thickening agent.

The composition can be used in a spray format, or as part of a gargle or mouthwash. A preferred format is as a sprayable liquid.

According to a second aspect of the present invention there is provided the use of a pharmaceutical composition as described in the first aspect of the invention for the treatment of sore throat.

According to a third aspect of the present invention there is provided a method of treating a sore throat using a formulation as described in the first aspect of the invention.

According to a fourth aspect of the present invention there is provided a method of reducing the irritation or burn associated with flurbiprofen comprising administering to an individual a composition in accordance with the first aspect of the present invention.

According to a fifth aspect of the present invention there is provided a method of improving the stability of flurbiprofen when in solution wherein the solution includes compounds bearing a hydroxyl group which do not act as a solvent and wherein the method includes the step of mixing the flurbiprofen with a cyclodextrin prior to addition of the compounds bearing a hydroxyl group.

Typically the solution containing the flurbiprofen is an aqueous solution.

Typically the method is used to form a composition in accordance with the first aspect of the present invention.

The present invention will now be illustrated by the following example embodiments in which.

EXAMPLE 1

1.683 g of flurbiprofen and 6.265 g of beta cyclodextrin (BCD) were weighed into a 100 ml volumetric flask. 50 ml of pH 7.4 buffer solution was added to the volumetric flask and shaken to suspend and wet the BCD and flurbiprofen. 1 M NaOH (aq) was added dropwise with vigorous stirring until the flurbiprofen and beta cyclodextrin dissolved fully. 6 ml of NaOH solution was required to dissolve the BCD and flurbiprofen. The solution was made up to 100 ml with purified water and mixed well. The solution was clear and colourless. The pH was measured and found to be pH 7.40 exactly.

Additional examples were prepared in a similar way. Details of these compositions are given below.

| Material Name | Example 2 (% w/w) | Example 3 (% w/w) | Example 4 (% w/w) | Example 5 (% w/w) |
| --- | --- | --- | --- | --- |
| Flurbiprofen | 1.62 | 1.62 | 1.62 | 1.62 |
| Beta Cyclodextrin | 6.04 | 6.04 | 4.228 | 4.228 |
| Disodium Hydrogen Orthophosphate | 3.1825 | 3.1825 | 3.1825 | 3.1825 |
| Citric Acid Monohydrate | 0.11655 | 0.11655 | 0.11655 | 0.11655 |
| Methyl p-hydroxybenzoate | 0.2187 | 0.2187 | 0.2187 | 0.2187 |
| Propyl p-hydroxybenzoate | 0.04374 | 0.04374 | 0.04374 | 0.04374 |
| Sodium Hydroxide | 0.24 | 0.24 | 0.24 | 0.24 |
| Mint Flavour | 0.20 | 0.20 | 0.20 | 0.20 |
| Cherry Flavour | 0.25 | 0.25 | 0.25 | 0.25 |
| Hydroxyethyl Cellulose | — | 0.20 | — | — |
| WS-23 | — | — | 0.10 | 0.10 |
| Sodium Saccharin | 0.05 | 0.05 | 0.05 | 0.05 |
| Hydroxypropyl Beta Cyclodextrin | — | — | 2.238 | — |
| Methyl Beta Cyclodextrin | — | — | — | 2.24 |
| Purified Water | 88.03851 | 87.83851 | 87.5125 | 87.51051 |
| TOTAL | 100.00 | 100.00 | 100.00 | 100.00 |

Figure 1:
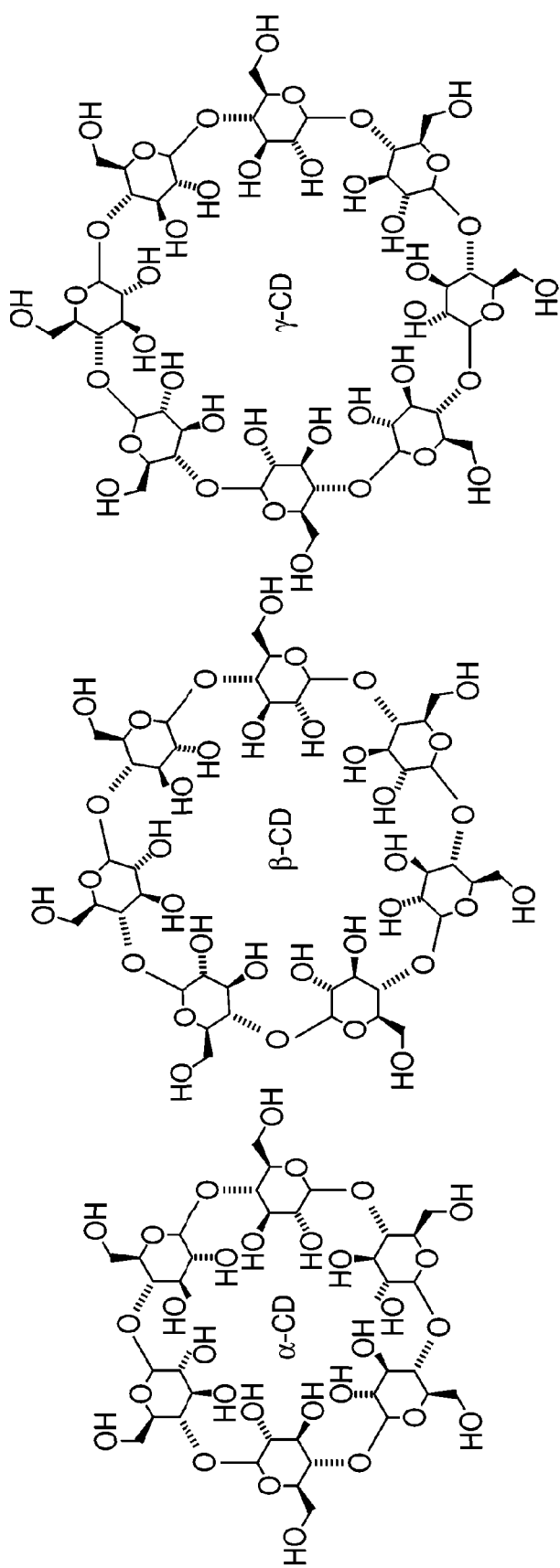
FIG. 1 illustrates α, β, γ cyclodextrin.
Figure 2:
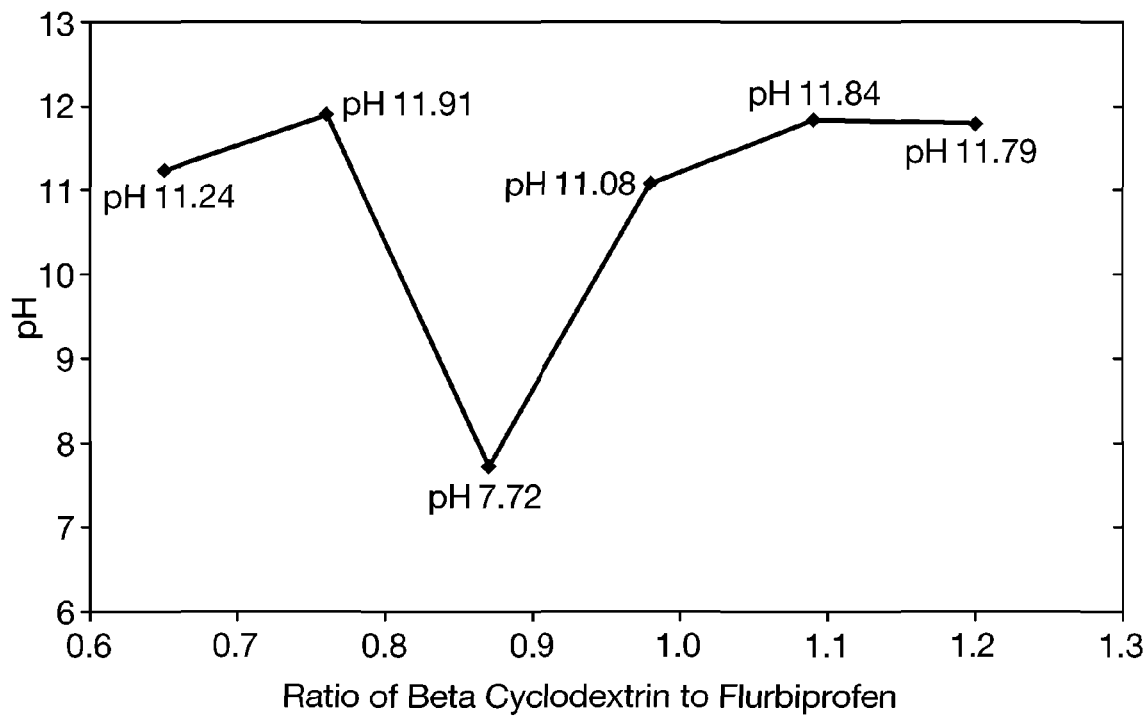
FIG. 2 illustrates the minimum pH required to achieve solution clarity for different beta cyclodextrin:flurbiprofen ratios at a flurbiprofen concentration of 14.58 mg/ml.

FIG. 2 illustrates the minimum pH required to achieve solution clarity for different beta cyclodextrin:flurbiprofen ratios and the effect of variation of the ratio of BCD to flurbiprofen on the minimum pH required as a result of gradual addition of 1M NaOH to obtain clarity. The required pH remains high until a ratio of about 0.75:1, at which point there is a dip in the threshold pH until the ratio is 1:1. The dip centres at a ratio of 0.87:1 BCD:Flurbiprofen. The flurbiprofen concentration is fixed at 8.75 mg per 600 μl.

Figure 3:
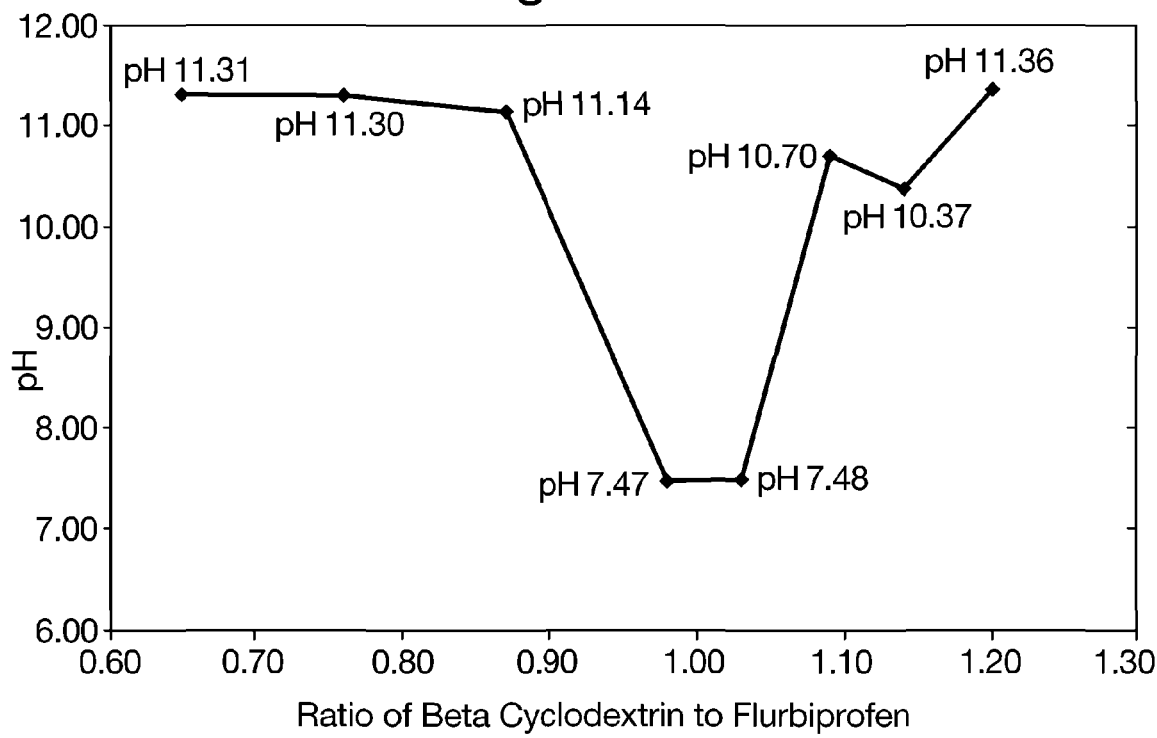
FIG. 3 illustrates the minimum pH required to achieve solution clarity for different beta cyclodextrin:flurbiprofen ratios at a flurbiprofen concentration of 31.25 mg/ml.

FIG. 3 illustrates the change in minimum required pH observed at a higher concentration of flurbiprofen. The dip in threshold pH centres at BCD:Flurbiprofen ratios Of 0.95:1 to 1.05:1.

Figure 4:
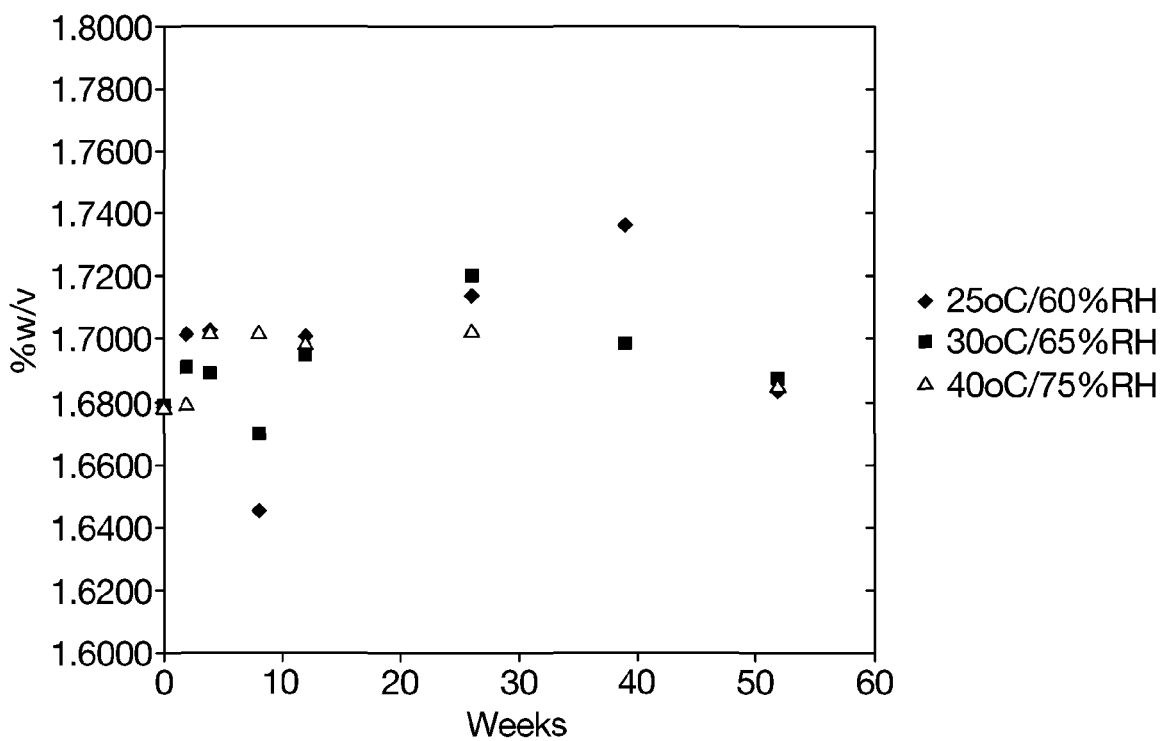
FIG. 4 illustrates degradation studies on example 4 of the present invention.
Figure 5:
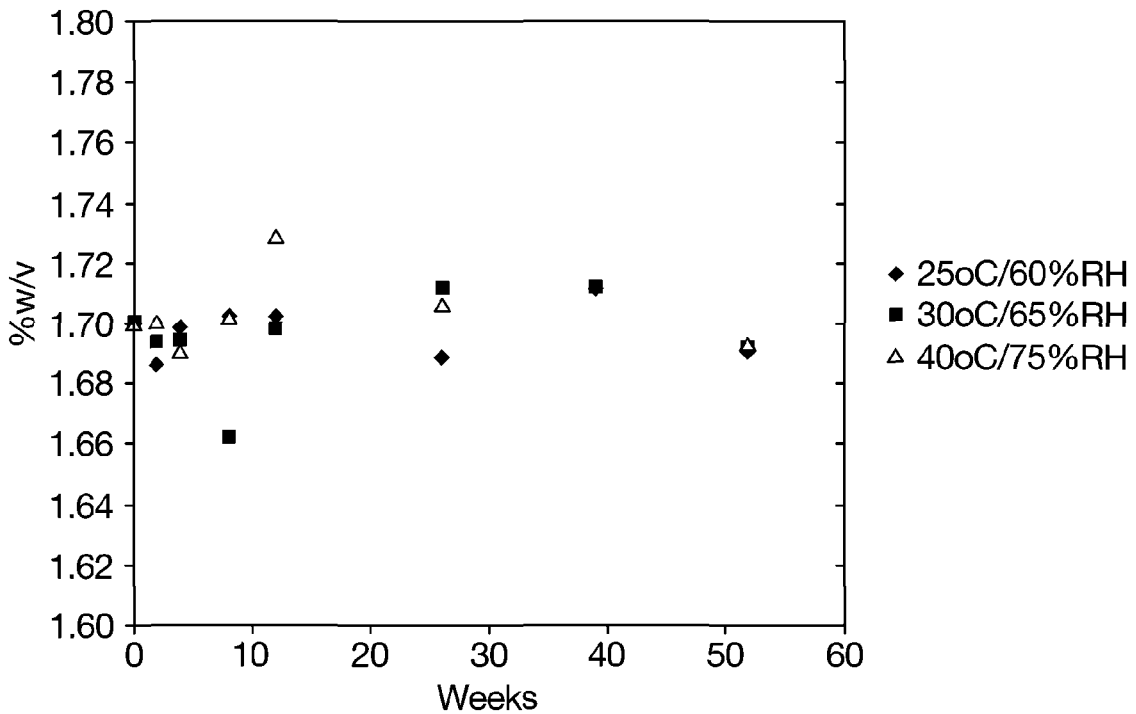
FIG. 5 illustrates degradation studies on example 5 of the present invention.

FIGS. 4 and 5 illustrated the improved stability for the compositions of examples 2 and 4 of the present invention. There is no significant degradation of flurbiprofen up to 52 weeks even at 40° C./75% RH. The results are given in the table below. Test compositions which contained ethanol showed degradation of between 10% and 14% within 2 weeks.

| | Time points | Example 4 Flurbiprofen Content (% mg per ml) | Example 2 Flurbiprofen Content (% mg per ml) |
| --- | --- | --- | --- |
| Storage Conditions | 0 | 1.6788 | 1.6997 |
| 25° C./60% RH | 2 | 1.7014 | 1.6863 |
| | 4 | 1.7029 | 1.6989 |
| | 8 | 1.6456 | 1.7027 |
| | 12 | 1.7011 | 1.7024 |
| | 26 | 1.7142 | 1.6886 |
| | 39 | 1.7365 | 1.7115 |
| | 52 | 1.6832 | 1.6908 |
| 30° C./65% RH | 2 | 1.6912 | 1.6939 |
| | 4 | 1.6889 | 1.6941 |
| | 8 | 1.6698 | 1.6622 |
| | 12 | 1.6945 | 1.6979 |
| | 26 | 1.7204 | 1.7117 |
| | 39 | 1.6982 | 1.7115 |
| | 52 | 1.6870 | 1.6922 |
| 40° C./75% RH | 2 | 1.6798 | 1.7004 |
| | 4 | 1.7028 | 1.6904 |
| | 8 | 1.7022 | 1.7019 |
| | 12 | 1.6992 | 1.7286 |
| | 26 | 1.7030 | 1.7060 |
| | 52 | 1.6845 | 1.6930 |

An advantage of the present invention is that there is provided a clear physically and chemically stable solution of flurbiprofen of sufficient concentration to be used in a throat spray product, where the clinically optimised dose of active pharmaceutical substance can be delivered/metered by a pump or other spray mechanism in a small volume of (concentrated) solution together with a method of preparation.

Such a solution does not exhibit the undesirable taste associated with compositions that are at higher pH, ie above about pH 8.

A further advantage of the present invention is that there is avoided the use of an alcohol as a co-solvent thus resulting in a composition with improved stability. The presence of an alcohol in a composition containing an NSAID with a carboxylic acid moiety results in the production of the corresponding ester. The compositions of the present invention do exhibit unexpected stability in the presence of other hydroxyl-containing compounds that are not solvents. For example, the flavour system used in the example embodiments does not result in higher levels of degradation of the flurbiprofen.

Further modifications and improvements can be made without departing from the scope of the invention described herein.

The invention claimed is:

1. A liquid composition comprising:
   1-5% w/w flurbiprofen;
   5-10% w/w of one or more $\alpha$, $\beta$, or $\gamma$ cyclodextrins;
   0.03-5% w/v of one or more aqueous buffers; and
   80-90% w/w water.

2. The liquid composition as claimed in claim 1, wherein the one or more $\alpha$, $\beta$, or $\gamma$ cyclodextrins are selected from the group consisting of methyl $\alpha$ cyclodextrin, hydroxyethyl $\alpha$ cyclodextrin, hydroxypropyl $\alpha$ cyclodextrin, dihydroxypropyl $\alpha$ cyclodextrin, methyl $\beta$ cyclodextrin, hydroxyethyl $\beta$ cyclodextrin, hydroxypropyl $\beta$ cyclodextrin, dihydroxypropyl $\beta$ cyclodextrin, methyl $\gamma$ cyclodextrin, hydroxyethyl $\gamma$ cyclodextrin, hydroxypropyl $\gamma$ cyclodextrin and dihydroxypropyl $\gamma$ cyclodextrin.

3. The liquid composition as claimed in claim 1, wherein the molar ratio of flurbiprofen to cyclodextrin is between 1:0.5 and 1:1.5.

4. The liquid composition as claimed in claim 3, wherein the molar ratio of flurbiprofen to cyclodextrin is between 1:0.7 and 1:1.1.

5. The liquid composition as claimed in claim 4, wherein the molar ratio of flurbiprofen to cyclodextrin is 1:0.87.

6. The liquid composition as claimed in claim 1, wherein the composition contains a concentration of flurbiprofen of no more than 3.2%.

7. The liquid composition as claimed in claim 6, wherein the concentration of flurbiprofen is 1.6% w/w.

8. The liquid composition as claimed in claim 6, wherein the concentration of flurbiprofen is 3.13% w/w.

9. The liquid composition as claimed in claim 1, wherein the one or more aqueous buffers are present at a concentration of about 0.1% to about 2.0% w/v.

10. The liquid composition as claimed in claim 1, wherein the one or more aqueous buffers are selected from the group consisting of phosphates, ascorbates, acetates, citrates, tartrates, lactates, succinates, amino acids and maleates.

11. The liquid composition as claimed in claim 1, wherein the one or more aqueous buffers are selected from the group consisting of disodium hydrogen orthophosphate, citric acid, and combinations thereof.

12. The liquid composition as claimed in claim 1, wherein the pH of the composition is from about 6 to about 9.

13. The liquid composition as claimed in claim 12, wherein the pH of the liquid composition is from about 7.2 to 7.6.

14. The liquid composition as claimed in claim 13, wherein the pH of the liquid composition is about 7.4.

15. The liquid composition as claimed in claim 1 further comprising one or more of pH adjusters, emulsifiers, dispersing agents, preservatives, sweeteners, and flavorants.

16. The liquid composition as claimed in claim 1 further optionally comprising 0-1% of one or more flavorants, 0-0.2% sweetener, and 0-0.5% preservatives.

17. The liquid composition as claimed in claim 1 further optionally comprising 0-0.5% thickening agent.

18. The liquid composition as claimed in claim 1, wherein the composition comprises a sprayable liquid.

19. The liquid composition as claimed in claim 1, wherein the $\alpha$, $\beta$, or $\gamma$ cyclodextrins are selected from the group consisting of natural cyclodextrins.

20. The liquid composition as claimed in claim 1, wherein the $\alpha$, $\beta$, or $\gamma$ cyclodextrins are selected from the group consisting of hydroxyethyl, 2- and 3-hydroxypropyl, their corresponding mixed ethers, and mixed ethers with methyl or ethyl groups selected from the group consisting of methyl-hydroxyethyl, ethyl-hydroxyethyl and ethyl-hydroxypropyl ethers of $\alpha$, $\beta$, $\gamma$-cyclodextrin.

21. The liquid composition as claimed in claim 1 further comprising a thickening agent selected from the group consisting of hydroxy ethyl cellulose, hydroxy propyl methyl cellulose, sodium carboxy methyl cellulose, and hydroxy propyl cellulose.

22. The liquid composition as claimed in claim 1 further comprising a base.

23. The liquid composition as claimed in claim 22, wherein the base comprises NaOH.

24. A method of treating a sore throat comprising:
   providing the liquid composition of claim 1; and
   spraying at least a portion of the liquid composition on the throat.

25. A method of reducing the irritation or burn associated with flurbiprofen comprising administering to an individual the liquid composition of claim 1.

26. A liquid composition comprising:
   1-5% w/v flurbiprofen;
   5-10% w/w of one or more $\alpha$, $\beta$, or $\gamma$ cyclodextrins;
   one or more aqueous buffers present in the range from about 0.03% to about 5.0% w/v;
   sodium saccharin; and
   80-90% w/w water.

27. The liquid composition as claimed in claim 26, wherein one or more of the aqueous buffers are present at a concentration of about 0.1% to about 2.0% w/v.

28. The liquid composition as claimed in claim 26, wherein one or more of the aqueous buffers are selected from the group consisting of phosphates, ascorbates, acetates, citrates, tartrates, lactates, succinates, amino acids and maleates.

29. The liquid composition as claimed in claim 26, wherein one or more of the aqueous buffers are selected from the group consisting of disodium hydrogen orthophosphate, citric acid, and combinations thereof.

30. The liquid composition as claimed in claim 26, wherein the pH of the composition is from about 6 to about 9.

31. The liquid composition as claimed in claim 26, wherein the pH of the liquid composition is from about 7.2 to 7.6.

32. The liquid composition as claimed in claim 26, wherein the pH of the liquid composition is about 7.4.

33. The liquid composition as claimed in claim 26, wherein one or more of the $\alpha$, $\beta$, or $\gamma$ cyclodextrins are selected from the group consisting of hydroxyethyl, 2- and 3-hydroxypropyl, their corresponding mixed ethers, and mixed ethers with methyl or ethyl groups selected from the group consisting of methyl-hydroxyethyl, ethyl-hydroxyethyl and ethyl-hydroxypropyl ethers of $\alpha$, $\beta$, $\gamma$-cyclodextrin.

34. The liquid composition as claimed in claim 26, wherein the concentration of flurbiprofen is no more than 3.2% w/v.

35. The liquid composition as claimed in claim 34, wherein the concentration of flurbiprofen is 1.6% w/v.

36. The liquid composition as claimed in claim 34, wherein the concentration of flurbiprofen is 3.13% w/v.

* * * * *